United States Patent [19]

Semkina et al.

[11] 4,211,624

[45] Jul. 8, 1980

[54] MATERIAL FOR PRODUCING PYROMETRIC REFRACTORY COMPONENTS, PYROMETRIC REFRACTORY COMPONENT, AND PROCESS FOR PRODUCING SAME

[76] Inventors: Novella V. Semkina, ulitsa Bljukhera, 71, korpus 1, kv. 38, Sverdlovsk; Galina S. Bokach, ulitsa Borovaya, 13, kv. 7, Kamyshlov Sverdlovskoi oblasti; Ivan V. Zinkovsky, Sevastopolsky prospekt, 12, korpus 3, kv. 9, Moscow, allof, U.S.S.R.

[21] Appl. No.: 16,967

[22] Filed: Mar. 2, 1979

[51] Int. Cl.² .................... C05B 35/48; G01N 27/58
[52] U.S. Cl. .................... 204/195 S; 106/57; 264/63; 264/66
[58] Field of Search .............. 106/57; 204/195 S, 1 S; 429/193; 123/119 E, 119 EC; 60/276; 324/29; 264/63, 66

[56] References Cited

U.S. PATENT DOCUMENTS 3,454,385  7/1969  Amero .................... 106/57 X

Primary Examiner—G. L. Kaplan
Attorney, Agent, or Firm—J. Harold Nissen

[57] ABSTRACT

A material for producing pyrometric refractory components contains the following ingredients: alumina—65 to 83%, titanium dioxide—6 to 10%, and zirconium dioxide—11 to 25%. Said pyrometric refractory components are produced from the above material. The process for producing said components comprises mixing of the starting ingredients, introduction of a plasticizing additive into the resulting mixture, moulding of the components, initial and final firing. The present invention permits minimizing the time lag of pyrometric refractory components used in a system intended for monitoring the temperature and oxidized state of molten metals, ensuring simultaneous monitoring of the temperature and oxidized state of molten metals and enhancing the reliability of pyrometric refractory components in operation, which provides for simple, rapid and inexpensive monitoring of metal melting parameters.

4 Claims, No Drawings

[4,211,624]

MATERIAL FOR PRODUCING PYROMETRIC REFRACTORY COMPONENTS, PYROMETRIC REFRACTORY COMPONENT, AND PROCESS FOR PRODUCING SAME

FIELD OF THE INVENTION

The present invention relates to the production of refractories, and more particularly to materials for producing pyrometric refractory components, to such components, and to processes for producing them.

The invention can find application in metallurgical production, in devices for measuring and monitoring the temperature and oxidized state of molten metals, in open-hearth furnaces, converters and electric steel-making furnaces.

BACKGROUND OF THE INVENTION

There is a widely known material for producing pyrometric refractory components (cf. British Pat. No. 1,281,718; 1973).

This material contains zirconium dioxide stabilized with calcium oxide. Pyrometric refractory components (solid electrolytes, protective caps, jackets, etc.) are made of this material in a conventional manner, in the shape of tubes with a sealed end.

The above material and process for producing pyrometric refractory components thereof, however, do not provide for their stability to rapid heating at elevated temperatures (above 1,000° C.) and reliability, i.e. a high ratio of the number of successfully tested pyrometric refractory components to the total number of tested components, in %.

Also known is a material for pyrometric refractory components (cf. U.S. Pat. No. 3,674,654; 1972) fabricated in a conventional manner from zirconium dioxide stabilized with beryllia.

This material and the associated process for producing pyrometric refractory components also fail to provide for adequate reliability and stability of such components heated to temperatures of up to 1,600° C.

Another known material for pyrometric refractory components manufactured in a conventional manner, is based on beta alumina (cf. U.S. Pat. No. 3,687,735). The disadvantages of this material and the associated process for producing pyrometric refractory components are the same as in the case of the previously mentioned two other materials and processes.

Yet another material for pyrometric refractory components is known (cf. U.S. Pat. No. 4,067,792), containing alumina, zirconium dioxide and titanium dioxide in the following ratio, % by weight:

| alumina | 85 to 95 |
|---|---|
| zirconium dioxide | 4 to 10 |
| titanium dioxide | 1 to 5. |

The material is used in producing pyrometric refractory components each being in the form of a tube with a sealed end, which are employed in devices for determining the oxidized state and temperature of molten metal.

The process for producing these pyrometric refractory components comprises mixing of finely divided ingredients: alumina, titanium dioxide and zirconium dioxide, introduction of a plasticizing additive into the resulting mixture, moulding of the component, drying at a temperature of 200° C., and firing at a temperature of 1,600° to 1,650° C., the ingredients being mixed in the following ratio, % by weight:

| alumina | 85 to 95 |
|---|---|
| titanium dioxide | 1 to 5 |
| zirconium dioxide | 4 to 10. |

However, the above material and process do not provide for the required high stability to rapid heating at temperatures ranging from 1,650° to 1,750° C., as well as for adequate overall and ionic conductivity of the material at low partial oxygen pressures in the ambient medium of $10^{-12}$ to $10^{-13}$ atm.

SUMMARY OF THE INVENTION

It is, therefore, an object of the present invention to provide a material and a process for producing pyrometric refractory components, ensuring high stability of said components to rapid heating at elevated temperatures and improved overall and ionic conductivity of the material at a partial oxygen pressure of $10^{-12}$ to $10^{-13}$ atm.

Another object of the invention is to provide a material and a process for producing highly reliable pyromatric refractory components.

These objects are attained by that in a material for producing pyrometric refractory components, containing alumina, zirconium dioxide and titanium dioxide, according to the invention, the above ingredients are in the following ratio, % by weight:

| alumina | 65 to 83 |
|---|---|
| titanium dioxide | 6 to 10 |
| zirconium dioxide | 11 to 25. |

These objects are also attained by that the pyrometric refractory component is, according to the invention, made of the above material.

Preferably, the pyrometric refractory component should, according to the invention, be made in the shape of a tube with a sealed end, the outside diameter-to-length ratio being 1:10 to 1:13 and the inside diameter-to-outside diameter ratio being 1:2 to 1:4.

It is expedient that in a process for producing pyrometric refractory components, comprising mixing of finely divided ingredients: alumina, titanium dioxide and zirconium dioxide, introduction of a plasticizing additive into the resulting mixture, moulding of the component, and firing thereof, according to the invention, the ingredients should be mixed in the following ratio, % by weight:

| alumina | 65 to 83 |
|---|---|
| titanium dioxide | 6 to 10 |
| zirconium dioxide | 11 to 25, | and the firing should be conducted in two steps: initial firing at a temperature of 1,200° to 1,300° C., aimed at complete removal of the plasticizing additive and partial strengthening of the component, and final firing at a temperature of 1,650° to 1,720° C., aimed at imparting the required strength to the component.

The invention permits minimizing the time lag of pyrometric refractory components used in a system intended for monitoring the temperature and oxidized state of molten metals, simultaneous monitoring of the temperature and oxidized state of molten metals, and enhancing the reliability of pyrometric refractory components in operation, which provides for simple, rapid and inexpensive monitoring of metal melting parameters, and the use of such components in steel production enables high yield of quality metal.

DETAILED DESCRIPTION OF THE INVENTION

The proposed material for producing pyrometric refractory components contains alumina, zirconium dioxide and titanium dioxide, taken in the following ratio, % by weight:

| | |
|---|---|
| alumina | 65 to 83 |
| titanium dioxide | 6 to 10 |
| zirconium dioxide | 11 to 25. |

The use of the above material permits producing strong components highly stable to rapid heating at elevated temperatures.

The introduction of a higher amount of zirconium dioxide (11 to 25%) improves the overall and ionic conductivity of the material, increasing them to 90–98%, at partial oxygen pressures of $10^{-12}$ to $10^{-13}$ atm, owing to the even distribution of zirconium dioxide on the surface of corundum crystals.

A further increase in the zirconium dioxide content leads to a lower stability of the material to rapid heating at elevated temperatures, as well as to a lower strength thereof.

At the same time, the introduction of a higher amount of titanium dioxide (6 to 10%) improves the sintering of the material when the latter is heated and permits producing dense (strong) components owing to the activization of the diffusion processes.

A further increase in the titanium dioxide content may result in poorer refractory properties of the material.

The basic ingredient, alumina, may be present in different amounts depending on the titanium dioxide and zirconium dioxide content.

The proposed material is used for producing pyrometric refractory components.

The process for producing pyromatric refractory components comprises mixing of dry finely divided ingredients: alumina, titanium dioxide and zirconium dioxide, which are mixed in the following ratio, % by weight:

| | |
|---|---|
| alumina | 65 to 83 |
| titanium dioxide | 6 to 10 |
| zirconium dioxide | 11 to 25, | introduction, into the resulting powder mixture having a specific surface of 1 m²/g, of a plasticizing additive, e.g. paraffin in an amount of 13 to 17% of the dry mixture weight, and its even distribution throughout the mixture. Then, moulded from the resulting thermoplastic paste are components, for example, in the shape of tubes whose one end is sealed in an appropriate manner. Thereafter, initial firing at a temperature of 1,200° to 1,300° C. is conducted to completely remove the plasticizing additive and partially strengthen the components, during which the material is partially sintered.

The final firing of the components is conducted at a temperature of 1,650° to 1,720° C. to impart them the required strength.

The initial high-temperature firing of the material ensures not only complete removal to the plasticizing additive, but also partial sintering of the material to an open porosity of 13 to 15%, higher strength of the intermediate product and, which is the most essential, permits zirconium dioxide particles to reach the surface of the emerging alumina (corundum) crystals.

Such an arrangement of the corundum and zirconium dioxide phases ensures, in turn, a higher stability of the material to rapid heating at elevated temperatures, as well as improved overall and ionic conductivity of the material.

The final firing at a higher temperature, i.e. at 1,650° to 1,720° C., results in dense (strong) components with a higher zirconium dioxide content owing to the active diffusion processes, and a higher stability of the components to rapid heating due to the formation of prismatic crystals 30 to 50 microns in cross section.

A pyrometric refractory component may be made in the form of a tube with a sealed end, the outside diameter-to-length ratio being 1:10 to 1:13 and the inside diameter-to-outside diameter ratio being 1:2 to 1:4.

These dimensional ratios are optimal and ensure high stability of the components to rapid heating at elevated temperatures and high reliability under conditions of rapid heating and constant temperature gradient within the range of 20° to 1,750° C.

For a better understanding of the invention, the following examples of its practical embodiment are given by way of illustration.

EXAMPLE 1

Pyrometric refractory components measuring 45×4×2 mm (length × outside diameter × inside diameter) was made of a material containing, % by weight:

| | |
|---|---|
| alumina | 83 |
| zirconium dioxide | 11 |
| titanium dioxide | 6. |
| The properties of the components were as follows: | |
| open porosity | 4.80% |
| apparent porosity | 3.75 g/cm³ |
| stability to rapid heating at 20 to 1,600° C. in molten steel 2 immersions reliability | 90% |
| overall conductivity $3.10^{-3}$ ohms$^{-1}$ . cm$^{-1}$ at 1,600° C. | |
| ionic conductivity at 1,600° C. and partial oxygen pressure of $10^{-12}$ atm | 80%. |

The components made of the above material and of the above dimensions exhibit a higher stability to rapid heating at a temperature of 1,600° C. in a molten metal, higher reliability and improved ionic conductivity at a partial oxygen pressure of $10^{-12}$ atm.

EXAMPLE 2

Pyrometric refractory components measuring 45×4×2 mm were made of a material containing, % by weight:

| | |
|---|---|
| alumina | 65 |

-continued

| | |
|---|---|
| zirconium dioxide | 25 |
| titanium dioxide | 10. |
| The properties of the components are as follows: | |
| open porosity | 3.68% |
| apparent porosity | 4.15 g/cm³ |
| stability to rapid heating at 20 to 1,600° C. in molten steel | 4 immersions |
| reliability | 100% |
| overall conductivity at 1,600° C. | $8.10^{-3}$ ohms$^{-1}$ . cm$^{-1}$ |
| ionic conductivity at 1,600° C. and partial oxygen pressure of $10^{-12}$ atm | 95%. |

The components exhibit a higher stability to rapid heating at elevated temperatures, higher reliability and improved overall and ionic conductivity at partial oxygen pressures of $10^{-12}$ to $10^{-13}$ atm.

EXAMPLE 3

Pyrometric refractory components measuring 40×4×1.4 mm were made of a material containing, % by weight:

| | |
|---|---|
| alumina | 78 |
| zirconium dioxide | 15 |
| titanium dioxide | 7. |
| The components feature the following properties: | |
| open porosity | 3.95% |
| apparent porosity | 3.87 g/cm³ |
| stability to rapid heating at 20 to 1,600° C. in molten steel | 2 immersions |
| reliability | 95% |
| overall conductivity at 1,600° C. | $5.10^{-3}$ ohm$^{-1}$ . cm$^{-1}$ |
| ionic conductivity at 1,600° C. and partial oxygen pressure of $10^{-12}$ atm | 85%. |

These components exhibit a higher stability to rapid heating at a temperature of 1,600° C. in a molten metal, higher reliability and improved ionic conductivity at a partial oxygen pressure of $10^{-12}$ atm.

EXAMPLE 4

Pyrometric refractory components measuring 40×4×2 mm were made of a material containing, % by weight:

| | |
|---|---|
| alumina | 77 |
| zirconium oxide | 15 |
| titanium oxide | 8. |
| The properties of these components are as follows: | |
| open porosity | 2.05% |
| apparent porosity | 4.07 g/cm³ |
| stability to rapid heating at 20 to 1,600° C. in molten steel | 2 immersions |
| reliability | 94% |
| overall conductivity at 1,600° C. | $5.10^{-3}$ ohms$^{-1}$ . cm$^{-1}$ |
| ionic conductivity at 1,600° C. and partial oxygen pressure of $10^{-13}$ atm | 85%. |

The components made of the above material and of the above dimensions exhibit a higher stability to rapid heating at a temperature of 1,600° C. in a molten metal, higher reliability and improved ionic conductivity at a partial oxygen pressure of $10^{-13}$ atm.

EXAMPLE 5

Pyrometric refractory components measuring 50×4×2 mm were made of a material containing, % by weight:

| | |
|---|---|
| alumina | 71 |
| zirconium dioxide | 20 |
| titanium dioxide | 9. |
| The components feature the following properties: | |
| open porosity | 2.80% |
| apparent porosity | 4.11 g/cm³ |
| stability to rapid heating at 20 to 1,600° C. in molten steel | 3 immersions |
| reliability | 97% |
| overall conductivity at 1,600° C. | $7.10^{-3}$ ohms$^{-1}$ . cm$^{-1}$ |
| ionic conductivity at 1,600° C. and partial oxygen pressure of $10^{-12}$ atm | 90%. |

The components made of the above materials and of the above dimensions exhibit a higher stability to rapid heating at a temperature of 1,600° C. in a molten metal, higher reliability and improved ionic conductivity at a partial oxygen pressure of $10^{-12}$ atm.

EXAMPLE 6

Pyrometric refractory components measuring 45×4×2 mm were made of a material containing, % by weight:

| | |
|---|---|
| alumina | 83 |
| zirconium dioxide | 11 |
| titanium dioxide | 6 | by the proposed process. The process comprises mixing of dry finely divided ingredients: alumina (83%), zirconium dioxide (11%) and titanium dioxide (6%), introduction, into the resulting power mixture having a specific surface of 1.1 m²/g, of paraffin in an amount of 14% of the dry mixture weight, and its even distribution throughout the mixture. Then, drawn from the resulting thermoplastic paste were components in the shape of tubes whose one end was sealed in an appropriate manner. Thereafter, initial firing at a temperature of 1,250° C. was conducted for 36 hours to completely remove the paraffin and partially strengthen the components. The final firing was conducted at a temperature of 1,650° C. for 42 hours to impart the required strength to the components.

The components produced by the above process feature the following properties:

| | |
|---|---|
| open porosity | 4.80% |
| apparent porosity | 3.75 g/cm³ |
| stability to rapid heating at 20 to 1,600° C. in molten steel | 2 immersions |
| reliability | 90% |
| overall conductivity at 1,600° C. | $3.10^{-3}$ ohms$^{-1}$ . cm$^{-1}$ |
| ionic conductivity at 1,600° C. and partial oxygen pressure of $10^{-12}$ atm | 80%. |

Thus, the components made by the above process exhibit a higher stability to rapid heating at a temperature of 1,600° C. in a molten metal, higher reliability and improved ionic conductivity at a partial oxygen pressure of $10^{-12}$ atm.

EXAMPLE 7

Pyrometric refractory components measuring 45×4×2 mm were made of a material containing, % by weight:

| | |
|---|---|
| alumina | 65 |
| zirconium dioxide | 25 |
| titanium dioxide | 10 | by the proposed process which comprises mixing of dry finely divided ingredients: alumina (65%), zirconium dioxide (25%) and titanium dioxide (10%), introduction, into the resulting powder mixture having a specific surface of 1.25 m²/g, of paraffin in an amount of 15% of the dry mixture weight, and its even distribution throughout the mixture. Then, drawn from the resulting paste were components in the shape of tubes whose one end was sealed in an appropriate manner. Thereafter, initial firing at a temperature of 1,300° C. was conducted for 36 hours to completely remove the paraffin and partially strengthen the components. The latter were subjected to final firing at a temperature of 1,720° C. for 42 hours, whereby they were imparted the required strength.

The components produced by this process feature the following properties:

| | |
|---|---|
| open porosity | 3.68% |
| apparent porosity | 4.15 g/cm³ |
| stability to rapid heating at 20 to 1,600° C. in molten steel | 4 immersions |
| reliability | 100% |
| overall conductivity at 1,600° C. | $8.10^{-3}$ ohms$^{-1}$ . cm$^{-1}$ |
| ionic conductivity at 1,600° C. and partial oxygen pressure of $10^{-12}$ atm | 95%. |

The components produced by the above process exhibit a higher stability to rapid heating at a temperature of 1,600° C. in a molten metal, higher reliability and improved ionic conductivity at a partial oxygen pressure of $10^{-12}$ atm.

EXAMPLE 8

Pyrometric refractory components measuring 50×4×2 mm were made of a material containing, % by weight:

| | |
|---|---|
| alumina | 71 |
| zirconium dioxide | 20 |
| titanium dioxide | 9 | by the proposed process which comprises mixing of dry finely dispersed ingredients: alumina (71%) zirconium dioxide (20%) and titanium dioxide (9%), introduction, into the resulting powder mixture having a specific surface of 1.25 m²/g, of paraffin in an amount of 15% of the dry mixture weight, and its even distribution throughout the mixture. Then, drawn from the resulting paste were components in the shape of tubes whose one end was sealed in an appropriate manner. Thereafter, initial firing at a temperature of 1,290° C. was conducted for 36 hours to completely remove the paraffin and partially strengthen the components. The latter were then subjected to final firing at a temperature of 1,680° C. for 42 hours to attain the required strength.

The components thus produced feature the following properties:

| | |
|---|---|
| open porosity | 2.8% |
| apparent porosity | 4.11 g/cm³ |
| stability to rapid heating at 20 to 1,600° C. in molten steel | 3 immersions |
| reliability | 97% |
| overall conductivity at 1,600° C. | $7.10^{-3}$ ohms$^{-1}$ . cm$^{-1}$ |
| ionic conductivity at 1,600° C. and partial oxygen pressure of $10^{-12}$ atm | 90%. |

Thus, the components produced by the proposed process exhibit a higher stability to rapid heating at a temperature of 1,600° C. in a molten metal, higher reliability and improved ionic conductivity at a partial oxygen pressure of $10^{-12}$ atm.

As can be inferred from the above, the present invention permits increasing the stability of pyrometric refractory components to rapid heating at elevated temperatures, improving the overall and ionic conductivity of the material at partial oxygen pressures ranging from $10^{-12}$ to $10^{-13}$ atm, and enhancing the reliability of these components in operation, which enables simple, rapid and inexpensive monitoring of metal melting parameters.

What is claimed is:

1. A material for producing pyrometric refractory components, comprising the following ingredients in, % by weight with the total percentage of such ingredients adding up to 100%:

| | |
|---|---|
| alumina | 65 to 83 |
| titanium dioxide | 60 to 10 |
| zirconium dioxide | 11 to 25 |

2. A pyrometric refractory component produced from said material claimed in claim 1.

3. A pyrometric refractory component as claimed in claim 2, made in the form of a tube with a sealed end, the outside diameter-to-length ratio being 1:10 to 1:13 and the inside diameter-to-outside diameter ratio being 1:2 to 1:4.

4. A process for producing pyrometric refractory components, comprising the following steps:

mixing of finely divided ingredients taken in the following ratio, % by weight:

| | |
|---|---|
| alumina | 65 to 83 |
| titanium dioxide | 6 to 10 |
| zirconium dioxide | 11 to 25; | with the total percentage of such ingredients adding up to 100%;

introduction of a plasticizing additive into the resulting mixture;

moulding of said components;

initial firing at a temperature of 1,200° to 1,300° C. to completely remove said plasticizing additive and partially strengthen said components;

final firing at a temperature of 1,650° to 1,720° C. to impart the required strength to said components.

* * * * *